United States Patent
Lucas et al.

(10) Patent No.: US 7,083,910 B2
(45) Date of Patent: Aug. 1, 2006

(54) PRESERVATION OF BLOOD PLATELETS WITH CITRATE

(75) Inventors: David Lucas, Lafayette, CA (US); Raleigh Carmen, Brentwood, CA (US)

(73) Assignee: Human Biosystems, Palo Alto, CA (US)

( * ) Notice: Subject to any disclaimer, the term of this patent is extended or adjusted under 35 U.S.C. 154(b) by 0 days.

(21) Appl. No.: 10/911,978

(22) Filed: Aug. 4, 2004

(65) Prior Publication Data

US 2005/0064381 A1   Mar. 24, 2005

Related U.S. Application Data

(60) Provisional application No. 60/492,491, filed on Aug. 4, 2003.

(51) Int. Cl.
*A01N 1/02*   (2006.01)
(52) U.S. Cl. .......................................................... 435/2
(58) Field of Classification Search ..................... 435/2
See application file for complete search history.

(56) References Cited

U.S. PATENT DOCUMENTS

| | | | |
|---|---|---|---|
| 4,059,967 A | | 11/1977 | Rowe et al. |
| 5,376,524 A | * | 12/1994 | Murphy et al. ................. 435/2 |
| 5,496,821 A | * | 3/1996 | Arduino .................... 514/228.8 |
| 5,753,428 A | * | 5/1998 | Yuasa et al. .................... 435/2 |
| 6,613,566 B1 | | 9/2003 | Kandler et al. |
| 2003/0158507 A1 | * | 8/2003 | Serebrennikov et al. ... 604/4.01 |

FOREIGN PATENT DOCUMENTS

| | | | |
|---|---|---|---|
| DE | 2929278 | | 1/1981 |
| JP | 54-103184 | * | 8/1979 |
| JP | 04001135 | | 1/1992 |
| WO | WO 91/17655 | | 11/1991 |
| WO | WO00/53008 | | 9/2000 |
| WO | WO03/000052 | | 1/2003 |

OTHER PUBLICATIONS

Young et al., "Reduction in Potassium Concentration Increases Platelet Sensitivity to Thrombin and ADP", FASEB Journal 6 (4): A1598 (1992).*
Leven et al., "Effects of Altered pH and Sodium Concentration on the Response of Megakaryocytes and Platelets to ADP", Thrombosis and Haemostasis 46 (1): 70 (981).*
Hernandez-Hernandez et al., Loss of phosphotyrosine phosphatase activity and changes in the tyrosine phosphorylation state of proteins after storage of sheep platelets in plasma or Seto solution at 4*C. Vox Sanguis 81 : 241-47 (2001).*
Database WPI: Section CH, Week 198524 Derwent Publication Ltd., London, AN 1985-144847, SU1124974A (As Sibe Biophys).
Brodthagen, U.A. et al. "Platelet cryopreservation with glycerol, dextran, and mannitol: Recovery of 5-hydroxytryptamine uptake and hypotonic stress response." *Cryobiology* (1985) vol. 22(1): Abstract only.
Smillie, J.A. et al. "Cryopreservation of human platelets with polyvinylpyrrolidone." *Transfusion* (1981) vol. 21(5): Abstract only.
Sputtek, A. et al. "Cryopreservation of human platelets with hydroxyethyl starch in a one-step procedure." *Cryo-Letters* (1987) vol. 8(4): 218-231.
Odink, J. et al. "Platelet preservation part 1. The use of decrease in light absorbance as a screening method in cryopreservation studies on human platelets." *Cryobiology*(1977) vol. 14(5): 519-528.

* cited by examiner

*Primary Examiner*—Sandra E. Saucier
(74) *Attorney, Agent, or Firm*—Wilson Sonsini Goodrich & Rosati

(57) ABSTRACT

Methods and compositions for preserving blood platelet suspensions which can be stored and preserved for extended periods of time are provided herein. The methods and compositions employ a mixture comprising blood platelets and one or more citrate salts. Such blood platelet mixtures may be cooled either rapidly or slowly and stored for several days prior to use in patients.

18 Claims, No Drawings

PRESERVATION OF BLOOD PLATELETS WITH CITRATE

REFERENCE TO RELATED APPLICATIONS

This patent application claims the benefit of the U.S. Provisional Patent Application Ser. No. 60/492,491 filed on Aug. 4, 2003, which is incorporated by reference in its entirety herein.

BACKGROUND

Platelets are one of the primary components of human blood. Blood is basically made up of plasma, red blood cells (erythrocytes), white blood cells (leukocytes), and platelets (thrombocytes). Platelets are produced in the bone marrow by large cells called megakaryocytes. It is commonly understood that platelets are actually not true cells, but are fragments of membrane and cytoplasm containing granules. More specifically, platelets comprise an outer membrane and cytoplasm from megakaryocytes which in turn contain granules, dense bodies, a dense tubular system, and mitochondria.

It is well recognized that platelets are an essential component of the blood clotting process and play a vital role in controlling bleeding. They adhere specifically to the endothelial cells and the basement membrane lining of damaged blood vessels, where they trigger and participate in hemostasis or clotting. In addition, inflammatory mediators may be released in response to this contact or in response to the mediators released by damaged tissue or other platelets. Important mediators released by platelets include serotonin and coagulation factors. Damaged blood vessels or other vascular breaches are repaired by platelets through such adhesion, and the ensuing response to this type of damage is further amplified by platelet secretions resulting in platelet aggregation and fibrin formation or a stabilized clot.

Platelet transfusions are an important aspect of the clinical management of patients with low numbers of platelets. Normal platelet counts range from about 150,000 to about 400,000 per cu/ml. A relatively low number of platelets may be due to cancer treatment and other reasons. Some patients may require transfusions for hemostasis, or whose platelets are defective in function. Platelets normally aggregate at a site of injury or vessel breakage as described above, and release a number of mediators to which other platelets respond in an amplifying biologic effect or coagulation cascade, which in turn stimulates other biologic effects. The normal, circulating platelet has a disc-shaped morphology. In response to a stimulus, the discs swell into spheres, and may further swell to a point where they eventually rupture. Concurrent with this observed change in shape, platelets release a variety of mediators, many of which are released by granules contained within the platelet. The morphology of platelets can be generally determined by microscopic observation. The ability of platelets to maintain their morphology can be tested by subjecting them to mild hypotonic conditions and following their return to disc shape as the membranes pump out excess water. This test is called hypotonic shock response (HSR) and ascertains the ability of the platelet membrane to remain intact during swelling of the platelet and to function by pumping water out of the platelet. Another test of platelet function monitors the change in platelet shape as platelets swell in response to a stimulus. This test is called extent of shape change (ESC). These methods are well known, and there is commercial instrumentation for determining these measures.

The process of preparing platelet transfusions typically begins with the separation of platelets as a product from whole blood. Bags of concentrated platelets in blood plasma may be obtained by apheresis or pheresis (centrifugal separation during the donor process while other components are returned to the donor) or by selective removal from whole blood after gravity or centrifugal sedimentation of blood cells. Preparation by centrifugation of whole blood collected in anticoagulant can be either with a slow spin that leaves platelets in suspension while removing red cells, followed by a faster spin to sediment the platelets from plasma, allowing resuspension in a reduced volume of plasma (slow/fast method producing platelet concentrate), or with a fast spin that sediments red cells and platelets, the platelets being in a buffy coat on top of the red cells, followed by removing that buffy coat layer along with an amount of plasma and doing a slow spin to remove remaining red cells from the suspended buffy coat (fast/slow method producing buffy coat platelets). Typically, sodium citrate is the anticoagulant used in making platelet preparations and the final concentration of citrate is up to about 15 mM in the platelet product in plasma.

It is very important to preserve platelets after their isolation from the body under suitable conditions that not only maintain the biological activity of the platelets, but also keep them suitable for subsequent clinical use. The average survival time for a platelet in the body after it leaves the bone marrow is eight to ten days. The average expected survival time for circulating platelets is four to five days, which is the average for an entire platelet population. Meanwhile, the current standard and approved method for platelet storage is in a platelet bag that is stored at room temperature for not more than five (5) days. This storage time is limited by the effects of metabolism, including changes in pH, the loss of clinical usefulness, and the risks from growth of small numbers of bacteria that may contaminate the preparation. Some clinicians apply even stricter criteria and decline to use platelets stored for more than three (3) days. The relatively short storage times and the risk of bacterial growth during such storage are major disadvantages and problems associated with current platelet storage methods.

Today, some platelets in suspension are also stored at reduced temperatures within normal refrigeration or freezing temperatures ranges. While cold temperature generally serves to suppress bacterial growth, platelets at refrigerator temperatures are known to become activated, change shape, lose function, and are cleared from the circulation if transfused. Thus, cold storage has been deemed to render platelets non-functional and of little clinical use. Other approaches for preserving platelets have also been reported, including cryopreservation at freezing temperatures in the presence of cryoprotectant such as DMSO. This freezing process is tedious, typically involving gradual lowering of temperature. The recovery of platelets from cryopreservation is also tedious and requires the removal of DMSO and/or other components prior to use in transfusion. Expected platelet recovery from the effects of freezing itself can be relatively low, and the yield is further reduced by subsequent washing in order to remove cryoprotectants or other agents. Satisfactory clinical use has not yet been reported for such platelet preservation techniques.

The present invention provides solutions and methods for cooling blood platelets to refrigerator temperatures and for storage of platelets at refrigerator temperatures for many days. The platelets stored using these methods remain functional and clinically useful.

SUMMARY OF THE INVENTION

The present invention describes methods and solutions for preserving blood platelets for, extended periods of time while retaining platelet functionality and clinical usefulness. The invention includes preparing a suspension of blood platelets by mixing the platelets with a citrate salt. Additional preservatives can also be added to the suspension, including, among others, carbohydrates, glycerol, and polyvinylpyrrolidone.

In some embodiments, the suspension can then be cooled to refrigerator temperatures and stored at these temperatures for long periods of time. The cooling can be accomplished by a variety of methods, including placing the suspension in an ice/water bath, placing the suspension in a refrigerator, and cooling the suspension instantly. In preferred embodiments, the preservation of the suspension is independent of the rate of cooling. The platelets can then be warmed and are ready for use or transfusion.

DETAILED DESCRIPTION OF THE INVENTION

The present invention describes improved methods and solutions for preserving blood platelets. The methods described herein can be used to extend the time for which platelets can be stored, while retaining their functionality and clinical usefulness. In one aspect of the invention, the blood platelets to be preserved are combined with a citrate salt to form a mixture. The blood platelets can be obtained by any method known in the art, including centrifugation and apheresis. The blood platelets can be obtained from humans or other animal species.

The citrate concentration in the platelet mixture is preferably about 37.5 mM. In other embodiments, the citrate concentration can be about 15 mM, about 22.5 mM, or about 52.5 mM. Higher or lower citrate concentrations can also be employed. Any citrate salt can be used, including potassium citrate and sodium citrate. More than one citrate salt may be present in the mixture. Preferably, when a mixture of citrate salts are used, about 30% or more, about 40% or more, or about 40% to about 80% of the citrate is in the form of potassium citrate.

In some embodiments, the citrate salt is not a sodium citrate. In other embodiments, the concentration of citrate salt used is at least 15 mM. In yet other embodiments, the blood platelets are combined with one or more citrate salts and preserved at cold temperatures and the preservation is not dependent of the cooling rate.

Additional substances can be added to the platelet mixture, either together or in any combination. Such substances can be carbohydrates like glucose, sucrose, or mannitol, or other compatible carbohydrates. The carbohydrates can comprise about 0.5% to about 2% or more of the mixture. Other additives such as glycerol may also be added to the mixture. The amount of glycerol used can be in the amounts of about 1% to about 2% of the mixture. Polyvinylpyrrolidone (10,000 to 40,000 molecular weight) may also be added to the mixture, preferably in amounts up to tolerable viscosity levels. In a preferred embodiment, the blood platelets are suspended in a solution containing about 30 mM to about 45 mM citrate, about 0.25% to about 0.75% glycerol, and about 0.5% to about 2.5% polyvinylpyrrolidone (average molecular weight 10,000 to 12,000).

The platelet mixture containing none, all, or any combination of the additives described above can be cooled by various methods, including placing the mixture in an ice/water bath, placing the mixture on the shelf of a refrigerator, or instantly cooling the mixture. One method of instantly cooling the mixture is by pouring the mixture into a cold aluminum-clad bag.

Cooling the mixture can be at the rate of about 0.3° C. per second, at about 1° C. to about 2° C. per minute, or even at about 0.2° C. per minute or slower. In some preferred embodiments, the preservation of the platelet mixture lacks dependence on a rate of cooling.

The mixtures described herein can be cooled to refrigerator temperatures. Refrigerator temperatures are preferably from about 2° C. to about 5° C., but can include temperatures from about 0° C. to about 7° C.

Once cooled, the platelets can be stored in a refrigerator for as long as desired. The length of storage can be 5 days, 7 days, 10 days, or longer. When needed for use, the platelets can be warmed to a temperature of about 20° C. or above, about 22° C. or above, about 37° C., or about 42° C. The platelets can then be used or infused.

The benefits of some embodiments of the invention may be demonstrated by counting the intact surviving platelets, and comparing this to the number of platelets before cooling, to provide a measure of the percentage of platelets that are recovered intact and not lost by rupturing or other consequences. The platelets can be assessed for maintaining disc morphology, e.g., by microscopic observation, to ascertain the percentage of platelets that remain as discs compared to those having changed into spheres or swollen into balloons. The function and viability of the platelets can be assessed with assays of membrane function to respond to hypotonic conditions (HSR) and shape change in response to an agonist (ESC). If the platelets are sufficiently robust and functional, they can revert from sphere to disc and increase functionality under normal physiologic conditions, for example, after transfusion.

Preferably, at least about 50%, about 60%, about 70%, about 80% or more of the platelets are recovered from platelet suspensions. In addition, preferably at least about 10%, about 20%, about 30%, about 50% or more of the platelets maintain their disc morphology and function for at least about 2 days, about 3 days, about 5 days, about 7 days, about 10 days, and preferably longer in cold storage using the methods and solutions of this invention. Preferably, a substantial portion of the platelets are functional and considered viable. Disc morphology and function are preferably maintained about 2 days, about 3 days, about 5 days, about 7 days, about 10 days, and longer in cold storage using the methods and solutions of this invention. Preferably, at least about 50%, about 60%, about 70%, about 80% or more of the platelets maintain disc morphology and function for at least about 2 days, about 3 days, about 5 days, about 7 days, about 10 days, and preferably longer in cold storage using the methods and solutions of this invention.

In one embodiment, about 30 ml of platelet concentrate obtained by apheresis is mixed with an equal volume of a solution composed of about 60 mM potassium citrate and about 2.4% glucose, with a pH of about 7.2. The suspension is cooled in an ice/water bath at about 0.3° C./second or by placing the bag on the shelf of a refrigerator where the cooling is at a rate of about 1° C./minute to about 2° C./minute. In another embodiment, the suspension is cooled rapidly by pouring it into a cold aluminum-clad bag that cools essentially instantly to about 4° C. Bags can be stored for about 5 days in a refrigerator and then warmed in a 37° C. bath. Platelets preserved using this technique retained about 25% to about 50% of their function as measured by HSR and about 10% to about 25% of their function as measured by ESC after storage at about 2° C. and warming to about 37° C.

In another embodiment, an equal volume of platelet concentrate obtained by apheresis is mixed with an equal volume of a solution composed of about 60 mM potassium citrate and about 1% glycerol, or with an equal volume of about 60 mM potassium citrate and about 1% glycerol and about 3.4% polyvinlylpyrrolidone (average molecular weight 10,000). Bags are handled and stored as noted above. The platelets stored in this manner showed swirling activity which is an indication of normal, disc morphology.

Also, blood platelets can be prepared from whole blood by standard centrifugation methods and the resulting platelet suspension in plasma is mixed with an equal volume of a solution comprised of about 60 mM potassium citrate and about 1% glycerol. The suspension is cooled to refrigerator temperature and stored for about 10 days. The suspension can be cooled to about 0° C. to about 7° C., preferably to about 2° C. to about 5° C. After the about 10-day storage, the suspension can be warmed to about 22° C., then to about 37° C. After cold storage for about 10 days, platelets preserved with this technique showed about 6% to about 13% normal disc morphology, HSR of 21, ESC of 1, and detectable swirling. Thus, using the techniques of the present invention, platelets can be stored for about 10 days or longer.

The methods described herein can be used in combination with methods and compositions described in PCT patent application No. PCTUS02/20878.

The following non-limiting examples are intended to demonstrate some of the preferable embodiments of the invention. It shall be understood that one skilled in the art will readily recognize that other alternative embodiments may be practiced in order to achieve the effects and benefits of the invention as described herein.

EXAMPLES

Storage of Platelets with Potassium Citrate

The following conditions were tested—using additive of 60 mM potassium citrate with 2.4% glucose as the reference, glycerol as a protectant in different concentrations in place of glucose, and PVP as an additive with potassium citrate, and the combination of glycerol with PVP. Bags 11–15 were stored in a refrigerator at 2° C. for 5 days.

| | |
|---|---|
| Bag #11 (All bags are PL 1240 or transfer bags) | 30 ml APC + 30 ml K-Cit(60 mM)/2.4% glu, rest 30 minutes at room temperature, and fast cool in ice bath, put in refrigerator at 2° C. |
| Bag #12 | 30 ml APC + 30 ml K-Cit(60 mM)/ 1% glycerol, rest 30 minutes at room temperature, and fast cool in ice bath, put in refrigerator at 2° C. |
| Bag #13 | 30 ml APC + 30 ml K-Cit(45 mM)/2% glycerol, rest 30 minutes at room temperature, and fast cool in ice bath, put in refrigerator at 2° C. |
| Bag #14 | 30 ml APC + 30 ml K-Cit(45 mM)/1% glycerol/3.4% PVP, rest 30 minutes at room temperature, and fast cool in ice bath, put in refrigerator at 2° C. |
| Bag #15 | 30 ml APC + 30 ml K-Cit(60 mM)/1% glycerol/3.4% PVP, rest 30 minutes at room temperature, and fast cool in ice bath, put in refrigerator at 2° C. |
| Control | Remainder of APC rocked at room temperature in a Baxter PL 1240 bag. |

K-Cit/glu2.4 (60 mM)(2.4% Glucose)
  60 mM KCit-Add 3.89 g potassium citrate (monohydrate) to 190 ml d.i. water, q.s. to 200 ml
  60 mM Cit Acid-Add 0.252 citric acid (monohyd) to 19 ml d.i. water, q.s. to 20 ml
  To 198 ml of the 60 mM KCit, add 4.8 g glucose and dissolve.
  Titrate to pH 7.2 by adding 60 mM citric acid to the 60 mM K Citrate (ca. 2 ml).
K-Cit (60 mM)/1% Glycerol
  60 mM KCit-use stock solution as described above
  60 mM Cit Acid-use stock solution as described above
  To 98 ml of the 60 mM KCit, add 1 g glycerol and mix.
  Titrate to pH 7.3 by adding 60 mM citric acid to the 60 mM K Citrate (ca. 1 ml).
K-Cit (45 mM)/2% Glycerol
  45 mM KCit-Add 2.92 g potassium citrate (monohydrate) to 195 ml d.i. water, q.s. to 200 ml
  45 mM Cit Acid-take 6.0 ml of the 60 mM citric acid, add 2.0 ml d.i. water, mix
  To 97 ml of the 45 mM KCit, add 2.0 g glycerol and mix.
  Titrate to pH 7.3 with 45 mM Citric Acid.
K-Cit (45 mM)/1% Glycerol/3.4% PVP
  45 mM KCit-use as made above
  45 mM Cit Acid-use as made above
  To 98 ml of the 45 mM K-Citrate, add 1.0 g glycerol and 3.4 g PVP-10 and mix.
  Solution was at pH 7.1 and no titration with 45 mM Citric Acid was needed.
K-Cit (60 mM)/1% Glycerol/3.4% PVP-10
  60 mM KCit-use as made above
  60 mM Cit Acid-use as made above
  To 95 ml of the 60 mM K-Citrate, add 1.0 g glycerol and 3.4 g PVP-10 and mix.
  Solution was at pH 7.2 and no titration with 60 mM Citric Acid was required.

The pHs and osmolarities of the solutions are provided below.

| | pH | mOsm/L |
|---|---|---|
| K-Cit(60 mM)/2.4% Glu | 7.2 | 305 |
| K-Cit(60 mM)/1% Glycerol | 7.3 | 289 |
| K-Cit(45 mM)/2% glycl | 7.3 | 364 |
| K-Cit(45 mM)/1% glycl/PVP3.4 | 7.1 | 303 |
| K-Cit (60 mM)/1% glycl/PVP3.4 | 7.2 | 339 |

APC was collected with Gambro separator and rested overnight at room temperature on a rocker. Total volume 257 ml containing 35 ml ACD-A.

Platelet count was $0.91 \times 10^6/\mu L$, ESC=22.8, HSR=90.0, swirl=10.

Bags were prepared and handled as noted above. Additives were at room temperature when added. Bags were stored at 2° C. for 5 days, static on a shelf in the refrigerator. When bags were removed from the refrigerator they were scored for swirling. The bag was put in a 37° C. water bath for 5 minutes and then into a 37° C. incubator for a total 90 minutes at 37° C.

Swirling was scored on a scale of 0–10 with 0=no swirling and 10=excellent.

| | | Swirling Score | | |
|---|---|---|---|---|
| Bag # | After additive | When put into refrigerator | When bags taken out of refrigerator | After 90 minutes at 37° C. |
| 11 | 10 | 10 | 0 | 0 |
| 12 | 10 | 10 | 1 | 0 |
| 13 | 10 | 10 | 1 | 0 |
| 14 | 10 | 10 | 2 | 1 |
| 15 | 10 | 10 | 2 | 0 |
| Control | 10 | | 8 | |

ESC and HSR were determined with a Chrono-Log SPA 2000.

| | ESC at start | ESC after 5 days | HSR at start | HSR after 5 days |
|---|---|---|---|---|
| Control bag | 22.8 | 14.9 | 90.0 | 54.7 |

ESC and HSR were determined on samples taken upon removal of bags from the refrigerator and again after 90 minutes incubation at 37° C.

| | ESC | | HSR | | Plt | |
|---|---|---|---|---|---|---|
| Bag # | Before 37° | After 37° | Before 37° | After 37° | Plt count ×10$^6$/μl | recovery % of start |
| 11 | 0.9 | 1.7 | 22.1 | 23.5 | | |
| 12 | 3.6 | 5.1 | 27.3 | 20.5 | | |
| 13 | 3.4 | 4.8 | 33.7 | 21.1 | | |
| 14 | 2.4 | 4.7 | 28.8 | 19.3 | | |
| 15 | 3.0 | 4.9 | 27.2 | 22.2 | | |

In this experiment, control platelets deteriorated during storage at room temperature. Interestingly, there seems to be more swirling before incubation at 37° C. than after, but swirling is greatest with PVP in the additive (bags 14 and 15). ESC was low in the reference test additive, and again the ESC was improved by presence of glycerol (bags 12, 13, 14, and 15). PVP did not seem to make a difference, except with swirling.

Sources of the Reagents:
Citric acid, monohydrate, Sigma C7129, lot 48F-0111
Glycerol, Glycerin USP, Bergen Brunswig, NDC 24385-033-94
Glucose, Sigma G5767, lot 121K08902
Potassium citrate Tribasic Monohydrate, Sigma P1722, lot 90K08241
Polyvinylpyrrolidone, Sigma PVP-10, lot 102K0153
ACD-A from Gambro
    Dextrose monohydrate 2.45 g/100 ml (per label)
    Sodium citrate dihydrate 2.2 g/100 ml
    Citric acid anhydrous 0.73 g/100 ml
    Calculation of Citrate Concentration
    Na Cit 22.0/294.1=74.8 mM
    Cit acid 7.3/192.1=38.0 mM
    Total 112.8 mM
    In the APC, 43×112.8/300=16.2 mM citrate in the APC Experiments Using K-Cit/glu2.4 Additive Five experiments were performed using the potassium citrate additive containing 60 mM citrate and 2.4% glucose at pH 7.1–7.2, 310 mOsm/L. This additive was added to an equal volume of platelet concentrate, giving final contributions from the additive of 30 mM citrate and 1.2% glucose. Since the platelet concentrate is about 15 mM citrate, the final citrate concentration during storage is about 37.5 mM.

As can be seen from the tables below, this additive allows platelets to be stored at 2° C. for 5 days and recovered with about 50% of the HSR activity and 25% of the ESC activity of the control platelets stored for 5 days at room temperature.

Fast cooling was done by swishing the bag in an ice/water bath achieving an overall rate of about 0.3° C./second. Slow cooling was done by putting the bag on the shelf in the refrigerator and was about 1° to 2° C./minute. Superfast cooling was done by running the platelet suspension into a cold aluminum-clad bag which chilled the suspension to 4° C. more or less immediately.

TABLE 1

HSR - Comparison of cold-stored platelets to room temperature (RT) control platelets.

| | | HSR at start | HSR after 5 days | HSR % of start | HSR % of control (5 d) |
|---|---|---|---|---|---|
| I | RT control | 75.0 | 58.8 | 78.4% | |
| | Fast cool | | 33.1 | 44.1% | 56.3% |
| | Slow cool | | Not done | | |
| II | RT control | 68.0 | 37.2 | 54.7% | |
| | Fast cool | | 24.3 | 35.7% | 65.3% |
| | Slow cool | | 18.1 | 26.6% | 48.6% |
| III | RT control | 60.5 | 37.2 | 61.5% | |
| | Fast cool | | 17.4 | 28.8% | 46.8% |
| | Slow cool | | 26.4 | 43.6% | 71% |
| IV | RT control | 59.3 | 51.3 | | |
| | Fast cool | | 28.6 | 48.2 | 55.8 |
| | Superfast | | 22.0 | 37.1 | 42.9 |
| V | RT control | 88.4 | 47.5 | | |
| | Fast cool | | 27.8 | 31.4 | 58.5 |
| | Superfast | | 26.4 | 29.9 | 55.6 |

TABLE 2

ESC - Comparison of cold-stored platelets to room temperature (RT) control platelets.

| | | ESC at start | ESC after 5 days | ESC % of start | ESC % of control (5 d) |
|---|---|---|---|---|---|
| I | RT control | 29.1 | 24.0 | 82.5% | |
| | Fast cool | | 6.4 | 22% | 26.7% |
| | Slow cool | | Not done | | |
| II | RT control | 24.6 | 17.7 | 69.5% | |
| | Fast cool | | 3.7 | 15% | 20.9% |
| | Slow cool | | 3.2 | 13% | 18.1% |
| III | RT control | 13.8 | 14.5 | 105% | |
| | Fast cool | | 5.8 | 42% | 40% |
| | Slow cool | | 5.0 | 36.2% | 34.5% |
| IV | RT control | 23.9 | 24.0 | | |
| | Fast cool | | 8.2 | 34.3 | 34.2 |
| | Superfast | | 7.5 | 31.4 | 31.2 |
| V | RT control | 38.7 | 20.3 | | |
| | Fast cool | | 6.4 | 16.5 | 31.5 |
| | Superfast | | 5.4 | 13.9 | 26.6 |

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A method of preserving blood platelets comprising forming a mixture, said mixture comprising a blood platelet concentrate and citrate, wherein said mixture which has a citrate concentration of about 30 mM to about 55 mM, and wherein said citrate preserves said blood platelets.

2. The method of claim 1 further comprising cooling said mixture.

3. The method of claim 2 wherein said cooling is performed by refrigerating said mixture or placing said mixture in an ice/water bath.

4. The method of claim 2 wherein said cooling is performed by placing said mixture in a cold aluminum-clad bag.

5. The method of claim 2 wherein said mixture is cooled to about 2° C. to about 5° C.

6. The method of claim 2 wherein said cooling is performed at a rate of about 0.3° C. per second, about 1° C. to about 2° C. per minute, or about 0.2° C. per minute.

7. The method of claim 2 wherein said mixture is cooled for about 5 days, about 7 days, or about 10 days.

8. The method of claim 1 wherein said platelets are obtained by apheresis or by centrifugation.

9. The method of claim 1 wherein said citrate is present at a concentration of about 30 mM to about 45 mM of said mixture.

10. The method of claim 1, wherein said mixture has a citrate concentration of about 45 to about 55 mM.

11. The method of claim 1, wherein said mixture has a citrate concentration of 37.5 mM.

12. The method of claim 1 wherein said mixture further comprises a carbohydrate.

13. The method of claim 12 wherein said carbohydrate is a glucose, a sucrose, a mannitol, or a combination thereof.

14. The method of claim 12 wherein said carbohydrate is present at a concentration of about 0.5% to about 2% of said mixture.

15. The method of claim 1 wherein said mixture further comprises glycerol.

16. The method of claim 15 wherein said glycerol is present at a concentration of about 1% to about 2% of said mixture.

17. The method of claim 1 wherein said mixture further comprises polyvinylpyrrolidone.

18. The method of claim 15 wherein said mixture further comprises polyvinylpyrrolidone.

* * * * *